US011311875B2

(12) United States Patent
Wahman

(10) Patent No.: US 11,311,875 B2
(45) Date of Patent: Apr. 26, 2022

(54) SAMPLE DEVICE FOR MOBILE WATER ANALYSIS

(71) Applicant: GOVERNMENT OF THE UNITED STATES AS REPRESENTED BY THE ADMINISTRATOR OF THE U.S. ENVIRONMENTAL PROTECTION AGENCY, Washington, DC (US)

(72) Inventor: David G. Wahman, Cincinnati, OH (US)

(73) Assignee: GOVERNMENT OF THE UNITED STATES AS REPRESENTED BY THE ADMINISTRATOR OF THE U.S. ENVIRONMENTAL PROTECTION AGENCY, Washington, DC (US)

(*) Notice: Subject to any disclaimer, the term of this patent is extended or adjusted under 35 U.S.C. 154(b) by 495 days.

(21) Appl. No.: 16/365,111

(22) Filed: Mar. 26, 2019

(65) Prior Publication Data

US 2019/0302088 A1 Oct. 3, 2019

Related U.S. Application Data

(60) Provisional application No. 62/761,547, filed on Mar. 29, 2018.

(51) Int. Cl.
*B01L 3/00* (2006.01)
*G01N 33/18* (2006.01)
*B65D 1/40* (2006.01)

(52) U.S. Cl.
CPC .......... *B01L 3/502715* (2013.01); *B65D 1/40* (2013.01); *G01N 33/1826* (2013.01); *G01N 33/1886* (2013.01)

(58) Field of Classification Search
CPC ..... B65D 1/40; B01L 3/502715; G01N 33/18; G01N 33/1886; G01N 33/1826
See application file for complete search history.

(56) References Cited

U.S. PATENT DOCUMENTS

| 9,012,234 B2 | 4/2015 | Lundgreen et al. .......... 436/165 |
| 9,052,302 B2 | 6/2015 | Lundgreen et al. |
| 2004/0004017 A1* | 1/2004 | Schmitt ................... G01F 19/00 206/459.5 |
| 2011/0223681 A1* | 9/2011 | Lundgreen ........ B01L 3/502715 422/68.1 |

* cited by examiner

*Primary Examiner* — Nathaniel J Kolb
(74) *Attorney, Agent, or Firm* — Stein IP, LLC

(57) ABSTRACT

The invention relates to a sample device that allows for simultaneous analysis of multiple liquid samples (e.g., drinking water samples). More specifically, the sample device is adapted for use with a mobile water analyzer, the sample device including an upwardly open receptacle divided into a plurality of separate upwardly open compartments separated by dividing walls. Each of the compartments is configured to contain a separate water sample, and the sample device is adapted to receive the inlet opening of a removable test element of a mobile water analyzer.

8 Claims, 5 Drawing Sheets

Prior Art

Prior Art

SAMPLE DEVICE FOR MOBILE WATER ANALYSIS

CROSS-REFERENCE TO RELATED APPLICATIONS

This application claims the benefit of priority to U.S. Provisional Application No. 62/761,547, filed Mar. 29, 2018 in the U.S. Patent and Trademark Office. All disclosures of the documents named above are incorporated herein by reference.

BACKGROUND OF THE INVENTION

1. Field of the Invention

The invention relates generally to the field of mobile water-analyzing systems and a method for determining an analyte in a water-sample. More specifically, the invention provides a sample device that will allow for multiple water samples to be simultaneously analyzed by a mobile-water analyzing system.

2. Description of the Related Art

Technology in the field of mobile water analysis has made advances in recent years. The older technology included photometric cuvette testing, which is performed manually by taking a water sample with a pipette and transferring the water sample into a cuvette that contains a reagent. The cuvette is closed, shaken to mix the water sample with the reagent, then inserted into a photometer for measurement.

Photometric cuvette technology can be time-consuming and prone to error. Accordingly, new technology has been developed that results in faster and more accurate analysis. Such technology incorporates the use of microfluidic-based removeable test elements (or Chemkeys) that contain reagents disposed in the sample line. This technology is exemplified by the Hach SL1000 Portable Parallel Analyzer. These relatively new portable analyzers allow for the simultaneous analysis of multiple water quality parameters (e.g., typically four parameters, such as free and total chlorine, monochloramine, nitrite, free and total ammonia) in a single sample. However, these analyzers do not provide a mechanism for analyzing multiple samples simultaneously.

Thus, there is a real need for a sample device that allows for multiple water samples to be simultaneously analyzed by a mobile water analysis instrument. Accordingly, the principle object of the invention is to provide such a sample device. Other objects will also be apparent from the following detailed description of the invention.

SUMMARY OF THE INVENTION

Broadly stated, the objects of the invention are realized, according to one aspect of the invention, by providing a sample device adapted for use with a mobile water analyzer, the sample device including an upwardly open receptacle divided into a plurality of separate, upwardly open compartments separated by dividing walls. Each of the compartments is configured to contain a separate water sample, and the sample device is adapted to receive the inlet opening of one or more removable test elements of a mobile water analyzer, each compartment adapted to receive one or more test elements. Advantageously, the sample device allows for the simultaneous analysis of a plurality of separate water samples.

In one embodiment of the invention, the sample device includes four separate compartments.

In another embodiment of the invention, the sample device includes five separate compartments, and one of the compartments is configured to receive a detector that detects the presence of a water sample.

In another embodiment of the invention, one or more of the compartments are configured to receive a detector that detects the presence of the water sample.

Each of the one or more removable test elements includes a microfluidic sample line. A reagent may be disposed in the microfluidic sample line.

The sample device may be made of a polymer and may be molded as a single piece unit.

In another embodiment of the invention, the dividing walls are removable, which allows for adjusting the number of compartments available in the sample device.

In an embodiment of the invention, each of the compartments has a capacity ranging from 20 ml to 60 ml.

The invention also embraces a method for simultaneously determining the concentration of an analyte in a plurality of separate water samples using the sample device described above which is adapted for use with a mobile water analyzer. The method may include the following steps: adding separate water samples to each of the compartments; immersing the inlet opening of each of the one or more removable test elements into the water samples in each of the compartments; and analyzing the water sample analyte with the mobile water analyzer.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
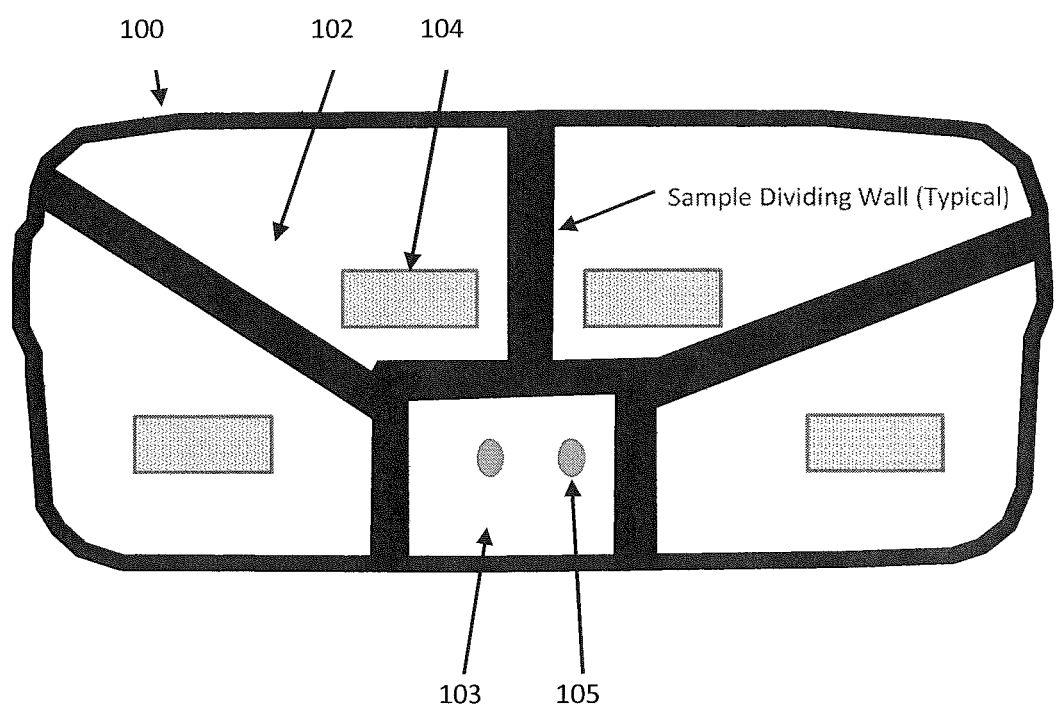
FIG. 1 shows a plan view of one embodiment of the sample device of the invention.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

The sample device of the invention allows for multiple water samples to be simultaneously analyzed by a mobile water analysis system. The sample device of the invention may be used with any mobile water analyzer. For example, in one embodiment, the invention is designed for use with the Hach SL 1000 Portable Parallel Analyzer (SL 1000).

The sample device of the invention provides several advantages over existing technology. First, various combinations of the number of samples and the number of parameter measurements may be achieved with the sample device of the invention. For example, in one embodiment, four different samples may be simultaneously analyzed for a single parameter. In another embodiment, two different samples may be simultaneously analyzed for two different parameters. The current sample device for the SL 1000 only provides the ability to analyze a single sample at a time for one to four parameters. The ability to measure multiple samples simultaneously would decrease the time required to analyze a given number of samples where less than four parameters are desired.

A second advantage of the present invention is that having the ability to perform simultaneous analysis on multiple samples allows the user to run duplicate samples simultaneously. This is important if the water quality is temporally transient (i.e., the water quality may change during the time required to perform analysis on the first sample and will therefore be different by the time the second sample is run for analysis).

A third advantage is that a smaller sample volume would be required perform analysis on a single sample. For example, only about 20 ml would be required, versus the 125 ml required using the existing sample device.

The sample device of the invention may be used, for example, in drinking water utilities and drinking water distribution systems, although the use of the device is not in any way limited to these areas.

In one embodiment of the invention, the same water sample is added to multiple (e.g., two) compartments with one or more of the water samples being treated using some method (e.g., pH adjustment, reagent addition). Analysis is then performed on the samples from each of the compartments.

Figure 2:
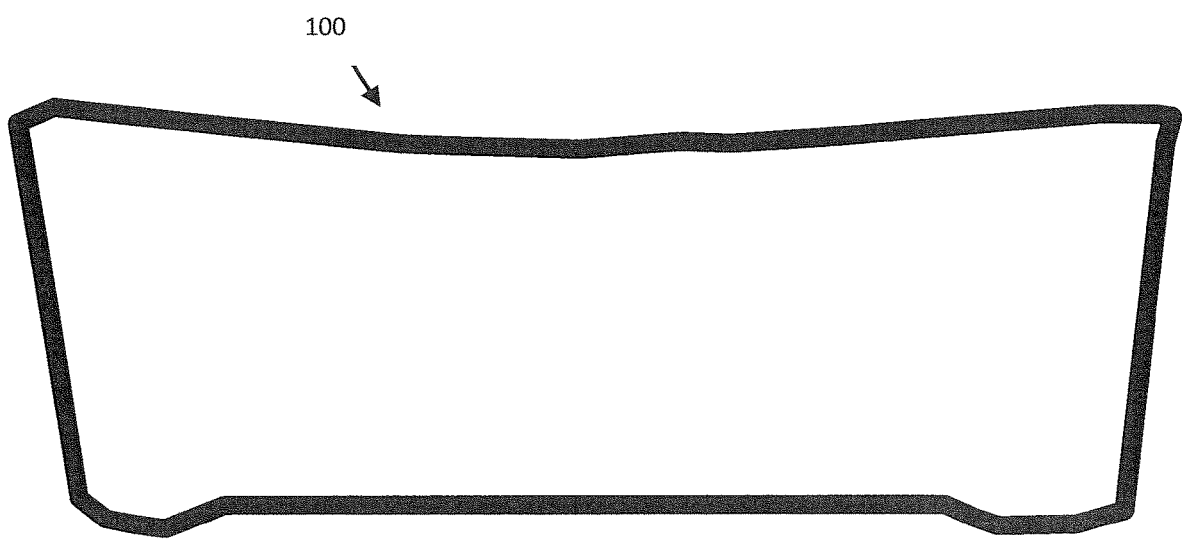
FIG. 2 shows a front view of one embodiment of the sample device of the invention.

Referring more specifically to the drawings, FIG. 1 provides a plan view of an embodiment of the sample device of the invention. FIG. 2 shows a front view of this embodiment of the invention. The sample device 100 incorporates five upwardly open compartments separated by dividing walls (or dividers). One compartment (103) is configured to receive a detector (105) that detects the presence of a water sample. The other four compartments (102) in this embodiment of the invention are designed to receive the inlet opening of a removable test element (104) from a mobile water analyzer (e.g., a Hach SL 1000 Portable Parallel Analyzer).

Figure 3:
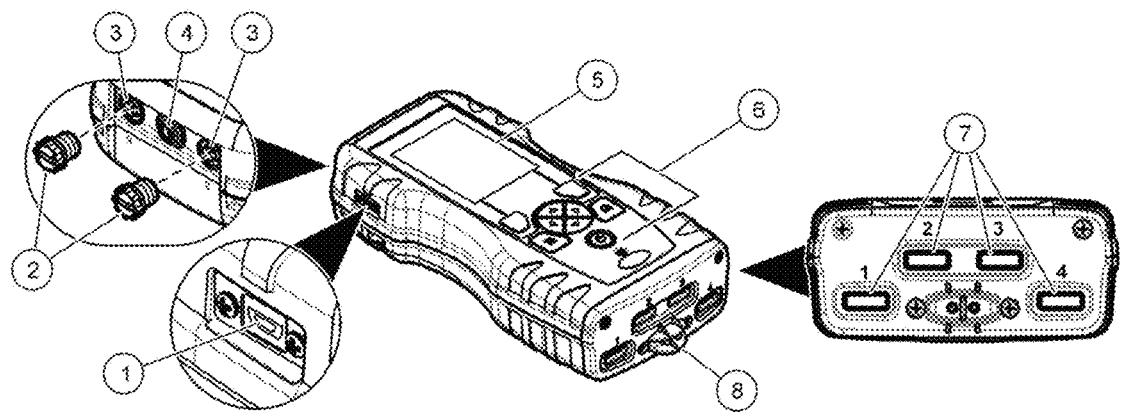
FIG. 3 provides a diagram of a Hach SL 1000 Portable Parallel Analyzer, a mobile water analyzer that may be used with the sample device of the invention.

FIG. 3 provides a diagram of the Hach SL 1000 Portable Parallel Analyzer. The diagram includes a legend that describes several of the key components of the analyzer. Notably, the sample detector 8 is able to detect the presence of the water sample in order to engage the pumping mechanism inside the analyzer to draw water into the microfluids within the removable test element. Chemkey slots 7 are the entry point in the analyzer for the removable test elements (or Chemkeys). It is the inlet openings of the removable test elements which are placed in the water samples in each compartment of the sample device. This introduces the sample water into the analyzer for analyte analysis.

Figure 4:
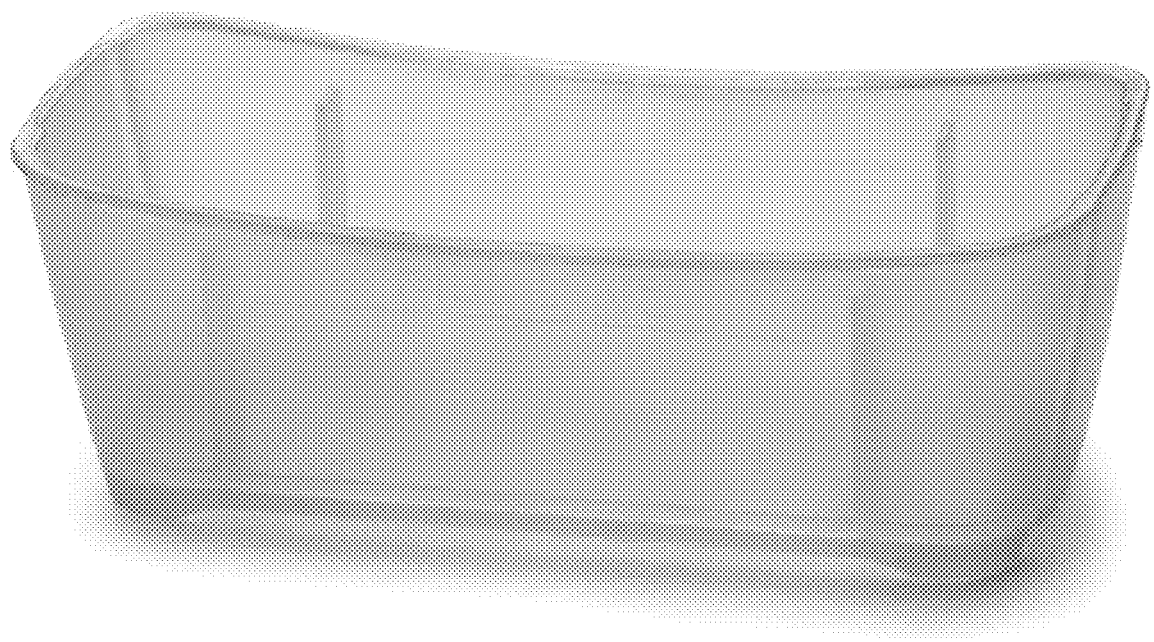
FIG. 4 provides a photograph of the current sample device for the Hach SL 1000 Portable Parallel Analyzer.

FIG. 4 is a photograph of the current sample device used in the Hach SL 1000 Portable Parallel Analyzer. It allows for only a single sample to be analyzed at a time and requires an approximate volume of 125 ml.

Figure 5:
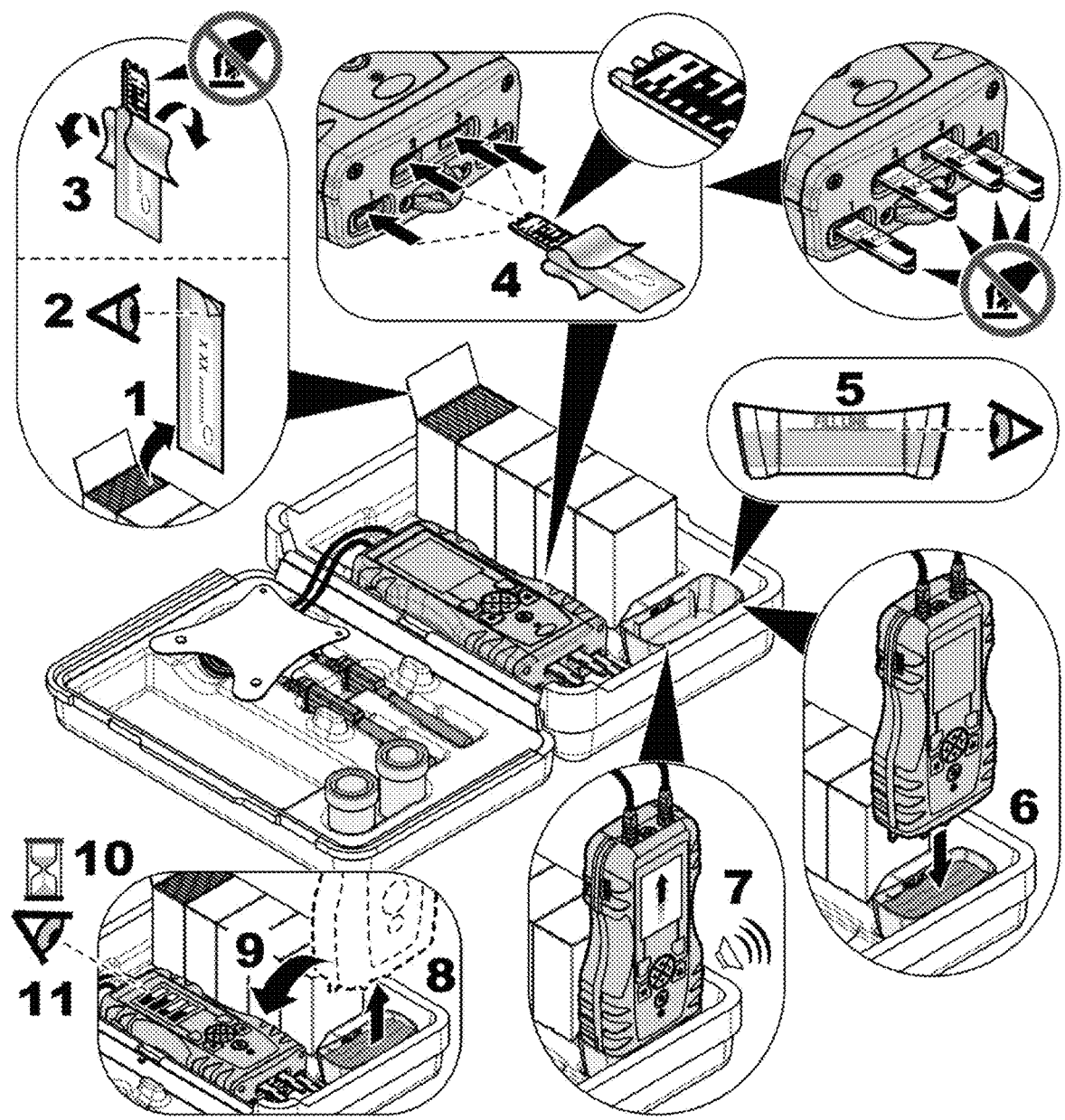
FIG. 5 provides a schematic of the Hach SL 1000 Portable Parallel Analyzer.

FIG. 5 is schematic of the Hach SL 1000 Portable Parallel Analyzer. Removable test elements (Chemkeys) are inserted into each of the four slots (1-4). The sample device is filled with a single sample (5). The analyzer is placed into the single sample (6) until an audible signal is provided (7), indicating that the sample has been extracted and the analyzer should be removed from the sample (8). The analyzer is then set aside (9) for a period of time for the single sample to process (10) before the sample result is presented by the analyzer (11). Another sample cannot be run until the sample result is presented by the analyzer.

In contrast the method of using the Hach SL 1000 analyzer described above, the sample device of the present invention advantageously allows for the analysis of more than one sample at one time. As discussed above, this may provide valuable benefits to the user.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A method for simultaneously determining a concentration of an analyte in a plurality of separate water samples using a sample device adapted for use with a mobile water analyzer, wherein the sample device comprises an upwardly open receptacle divided into a plurality of separate, upwardly open compartments separated by dividing walls, each of the compartments is configured to contain a separate water sample, and the sample device is adapted to receive the inlet opening of one or more removable test elements of a mobile water analyzer, each compartment adapted to receive one or more test elements, the method comprising:
adding separate water samples to each of the compartments;
simultaneously immersing the inlet opening of each of a plurality of the one or more removable test elements into the water samples in each of the compartments; and
simultaneously analyzing the water sample analyte in each of the compartments with the mobile water analyzer.

2. The method of claim 1, further comprising the step of performing a treatment step on the water samples in one or more compartments prior to immersing the inlet opening of each of the one or more removable test elements into the water samples.

3. The method of claim 2, wherein the treatment step includes at least one of pH adjustment and reagent addition.

4. The method of claim 1, wherein the analyzing comprises simultaneously analyzing different water quality parameters in the water sample analyte in each of the compartments.

5. The method of claim 1, wherein the analyzing comprises simultaneously analyzing the same water quality parameter in the water sample analyte in each of the compartments.

6. The method of claim 1, wherein the separate water samples are a single water sample split into each of the separate compartments.

7. The method of claim 6, wherein the analyzing comprises simultaneously analyzing the split water sample in each of the separate compartments.

8. The method of claim 1, further comprising:
detecting whether one of the compartments contains one of the water samples prior to analyzing the water sample analyte with the mobile water analyzer.

\* \* \* \* \*